United States Patent
Paufique (10) Patent No.: US 11,564,880 B2
(45) Date of Patent: Jan. 31, 2023

(54) METSCHNIKOWIA REUKAUFII EXTRACT AND USE IN COSMETICS

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 36 days.

(21) Appl. No.: 16/966,153

(22) PCT Filed: Jan. 30, 2019

(86) PCT No.: PCT/EP2019/052252
§ 371 (c)(1),
(2) Date: Jul. 30, 2020

(87) PCT Pub. No.: WO2019/149754
PCT Pub. Date: Aug. 8, 2019

(65) Prior Publication Data
US 2021/0059928 A1   Mar. 4, 2021

(30) Foreign Application Priority Data
Jan. 31, 2018 (FR) ..................... 1870099

(51) Int. Cl.
*A61K 8/99* (2017.01)
*A61K 8/04* (2006.01)
*A61Q 17/00* (2006.01)
*A61Q 19/08* (2006.01)

(52) U.S. Cl.
CPC ............ *A61K 8/99* (2013.01); *A61K 8/042* (2013.01); *A61Q 17/005* (2013.01); *A61Q 19/08* (2013.01); *A61K 2800/10* (2013.01); *A61K 2800/78* (2013.01)

(58) Field of Classification Search
CPC ........... A61K 36/06; A61K 8/64; A23L 31/10; A23L 31/15; A23L 33/18
See application file for complete search history.

(56) References Cited

U.S. PATENT DOCUMENTS

2013/0274221 A1* 10/2013 Paufique ............. C07H 3/06
514/54

FOREIGN PATENT DOCUMENTS

| EP | 1065276 A1 | 1/2001 | |
|---|---|---|---|
| EP | 2727579 A1 | 5/2014 | |
| FR | 3008891 A1 | 1/2015 | |
| WO | WO-2017195870 A1 * | 11/2017 | ............. C12P 13/24 |
| WO | WO2017195870 A1 | 11/2017 | |

OTHER PUBLICATIONS

Li et al (Appl Biochem Biotechnol, 2009, vol. 159, pp. 119-132) (Year: 2009).*
Dasgupta et al (Plos One, 2016, vol. 11, pp. 1-26) (Year: 2016).*
WO 2017/195870A1 (WIPO English translation, downloaded in Dec. 2021) (Year: 2021).*
Kenshi et al (European Journal of Dermatology, 2008, vol. 18, pp. 11-21) (Year: 2008).*
Sitepu et al., "Oleaginous yeasts for biodiesel: Current and fugure trends in biology and production", Biotechnololgy Advances, GB, Nov. 1, 2014, pp. 1336-1360, vol. 32, No. 7.
Turkel et al., "Isolation and characterization of new Metschnikowia Pulcherrima Strains as Producers of the Antimicrobial Pigment Pulcherrimin", Producers of Antimicrobial Pigment Pulcherrimin, Jan. 8, 2009, pp. 405-410.

* cited by examiner

*Primary Examiner* — Mark V Stevens
(74) *Attorney, Agent, or Firm* — Greer, Burns & Crain, Ltd.

(57) ABSTRACT

The invention relates to a cosmetic active ingredient comprising at least one *Metschnikowia reukaufii* extract, and the use of same for the cosmetic treatment of the skin, in particular for improving the radiance of the complexion by acting on the skin microbiota. The active ingredient is effective on mature skin. The invention also concerns compositions comprising the cosmetic active ingredient and a cosmetic method for treating the skin using these compositions.

13 Claims, 1 Drawing Sheet

METSCHNIKOWIA REUKAUFII EXTRACT AND USE IN COSMETICS

CROSS-REFERENCE TO RELATED APPLICATIONS

This application is the U.S. National phase application corresponding to PCT/EP2019/052252 which was assigned an international filing date of Jan. 30, 2019 and associated with publication WO 2019/149754 A1 and which claims priority to French patent application FR 1870099 filed on Jan. 31, 2018, the disclosures of which are expressly incorporated herein by reference.

TECHNICAL FIELD

The present invention relates to an extract of a specific yeast and to its use in cosmetics, in particular for its capacity to act on the skin microbiota and specifically on the microbiota of mature skin.

BACKGROUND

The skin coexists with many bacterial communities. Studies aimed at analyzing the interactions between the skin and its microbiota have multiplied in recent years and consumers are informed and educated on the benefits of bacteria and the importance of preserving this flora. Indeed, skin microbiota regulated on the surface of the skin influences immunity, nutrition and defense against pathogenic attacks. Thus, this symbiosis between the skin and its microbiota is beneficial and essential to its beauty. Unfortunately, under certain conditions, this fragile balance can be upset, which leads to the appearance of cosmetic disorders in the skin. This is the case in particular when skin ages, which causes an imbalance in the skin flora, which is responsible for the deterioration of the quality of the skin and in particular a dull complexion. The object of the invention is that of providing a solution capable of acting on the skin microbiota, in particular mature skin, in order to rebalance it and thus improve the quality of the skin, specifically the radiance of the complexion.

SUMMARY

To respond to this, the invention relates to the use of a particular yeast, *Metschnikowia reukaufii*.

*Metschnikowia reukaufii* is the dominant and specialist species of floral nectars. Having a remarkable metabolism, it has developed exceptional adaptation properties to this very selective and ephemeral substrate. It can be found in the nectar of different plants, and in particular in that of the emblematic, refined and very nectariferous plant: *Hoya Carnosa*. This plant, also called porcelain flower due to its bright flowers, has an incredible varnished and pearly appearance, and is a wonderfully shaped flower. In the extremely rich world of the Hoya, this plant has favored the feature of nectar to ensure its attractiveness. Every day, the porcelain flower therefore produces a veritable shower of nectar inhabited by microorganisms which provides protection and regeneration.

*Metschnikowia reukaufii* has never been used in cosmetics, and surprisingly, according to the invention, it makes it possible to improve the quality of the skin, in particular the radiance of the complexion, in particular by acting on the balance of the skin microbiota.

One object of the invention is therefore a cosmetic active ingredient comprising at least one *Metschnikowia reukaufii* extract, and the use of this active ingredient or of a composition containing said ingredient for a cosmetic treatment for topical application to the skin.

The invention also relates to cosmetic compositions comprising at least one *Metschnikowia reukaufii* extract, and a cosmetic method for treating the skin for an effect of improving and/or enhancing the radiance of the complexion, said method consisting of the topical application to the skin of such a composition.

Other characteristics and advantages will emerge from the detailed description of the invention which follows, with reference to the appended figures. in which:

DETAILED DESCRIPTION

Definitions

Within the meaning of the invention, "cosmetic active" or "cosmetic active ingredient" mean at least one molecule, preferably a set of molecules having a cosmetic effect on the skin, in particular on the skin cells. It is not an active ingredient for stabilizing a composition.

Within the meaning of the invention, "*Metschnikowia reukaufii*" means any yeast bearing this classification from the Metschnikowiaceae family, whether it comes from a porcelain flower or another plant. It can also be referred to by the synonymous names, *Metschnikowia zygota, Nectaromyces cruciatus, Nectaromyces reukaufii* and *Anthomyces reukaufii*. This term excludes genetically modified yeasts.

Within the meaning of the invention, "*Metschnikowia reukaufii* extract" means any extract derived from *Metschnikowia reukaufii* yeast, obtained by a method of extracting the native molecules of the yeast or a method of transforming (for example by means of hydrolysis) the native molecules of the yeast. The supernatant derived from the yeast culture means any molecule excreted by the yeast and any molecule of the cell wall of the yeast. Within the meaning, the term "*Metschnikowia reukaufii* extract" excludes yeast culture media.

Within the meaning of the invention, "protein fraction" or "peptide compounds" of the *Metschnikowia reukaufii* hydrolyzate mean all of the proteins and/or peptides present in the *Metschnikowia reukaufii* extract "*Metschnikowia reukaufii* hydrolyzate,*"* within the meaning of the invention, means any extract derived from the *Metschnikowia reukaufii* yeast, obtained by a method comprising at least one step of enzymatic or chemical hydrolysis.

"Mature skin" means skin of an age greater than or equal to 45 years old.

Within the meaning of the invention, "atomization support" means a neutral additive which can be added to a solution during spray drying.

The invention therefore relates to a cosmetic active ingredient comprising at least one *Metschnikowia reukaufii* extract.

Preferably, the *Metschnikowia reukaufii* extract comprises at least peptides.

Preferably, the *Metschnikowia reukaufii* extract comprises peptides having a molecular weight of less than 5000 Da, preferably less than 3500 Da, very preferably less than 2000 Da. These peptides play an important role in the effectiveness of the active ingredient according to the invention, in particular on the expression of HBD3 which is a marker of the immune barrier function of the skin.

Preferably, the peptides having a molecular weight lower than 3500 Da represent at least 90 wt.% of the protein fraction of the extract, even more preferably the peptides having a molecular weight lower than 2000 Da represent at least 60 wt.% of the protein fraction of the extract.

In the extract, the protein fraction represents at least 20 wt.% of dry matter of the extract, preferably between 20 and 60%.

The content of peptide compounds in the extracts according to the invention is determined by the LOWRY method (Lowry et al., Protein measurement with the folin reagent, J. Biol. Chem., 193, 265, 1951) or by the determination of total nitrogen according to the KJELDAHL method (reference: Official method of analysis of the AOC, 12th ed. W Horwitz, ED, New York, 15-60, 1975). Preferably, the content is determined according to the KJELDAHL method.

The extract according to the invention can also comprise other constituents, specifically sugars and/or minerals.

Preferably, the sugars, when present, represent less than 30 wt.% of dry matter of the extract. Preferably, the sugars present in the extract according to the invention are oligosaccharides and polysaccharides having molar masses of between 180 and 9000 Da (i.e. a degree of polymerization greater than 1 and less than 50), preferably having molar masses ranging between 180 and 2520 Da, (i.e. a degree of polymerization greater than 1 and less than 14). Preferably sugars comprise glucose and mannose in the form of oligosaccharides having an average molar mass of 557 Da.

The sugar content in the extract can be determined by the DUBOIS method (Dubois M. et al., *Analytical chemistry*, 28, 3, 350-356, 1956).

The minerals, when present in the extract, are preferably in particular potassium, sodium, chlorine, and phosphorus. Analysis of the minerals constituting the ash of the extract according to the invention can be carried out by optical emission spectrometry (ICP/OES) and the determination of the chloride ions can be carried out by means of silver nitrate titration. Preferably, the ash rate ranges between 20 and 60 wt.% of dry matter of the extract, even more preferably between 25 and 45%.

The crude ash content can be determined by weighing the residues from the incineration of the samples of the extract according to the invention at 550° C. in an electric muffle furnace. The extract according to the invention can be obtained by any type of extraction or transformation method of the native yeast molecules. Preferably, the extract is an aqueous extract. Preferably, the extract is a hydrolyzate, i.e. it is obtained by hydrolysis of the yeast. It can be obtained by chemical (acidic or basic) or enzymatic hydrolysis. Preferably, the extract according to the invention is an enzymatic hydrolyzate.

The active ingredient according to the invention can be in solid form or in liquid form. When it is in liquid form, the active ingredient according to the invention is preferably constituted by the extract as described above. It is usually in the form of a clear liquid which has a weak odor and a yellow color. It can however be discolored by any method known to a person skilled in the art.

When it is in solid form, the active ingredient according to the invention is preferably constituted by the extract as previously described and by a support selected from maltodextrin, acacia gum, soy lecithin or isomalt. According to one particularly suitable embodiment, the extract represents at least 25 wt.% of the active ingredient.

The extract constituting the active ingredient according to the invention can be obtained by any suitable method. Preferably, it is obtained by a method comprising a step of enzymatic hydrolysis, in particular at least one step of enzymatic hydrolysis of proteins, i.e. a hydrolysis carried out enzymatically by means of proteolytic enzymes. They may, for example, be proteases of plant origin or derived from microorganisms.

Prior to the method for obtaining the extract as such, it is necessary to produce the biomass of *Metschnikowia reukaufii*. This step is carried out depending on the type of yeast culture in a medium suitable for their development, in a conventional manner for a person skilled in the art. Before cultivation, it is possible to take the yeast and isolate it, preferably from flower nectar, in particular from nectar from the porcelain flower.

Once the biomass has been obtained, an extraction is carried out with a view to obtaining active molecules, preferably this extraction can contain at least one hydrolysis. According to a particularly suitable embodiment, the active ingredient is obtained by implementing the following steps:

solubilization of *Metschnikowia rekauffi* yeasts in water, preferably at least 50 g/l;
separation of the soluble and insoluble phases by decantation in order to recover the soluble phase;
filtrations;
sterilizing filtration.

A hydrolysis step, preferably enzymatic hydrolysis, and even more preferably hydrolysis using a protease, can be envisaged in the method for producing the active ingredient according to the invention. This step is preferably carried out after solubilization and before phase separation. The method can possibly comprise a step of heat treatment of the extract, in particular to eliminate the residual enzymatic activities. This step is preferably carried out before the phase separation step, and when there is a hydrolysis step, after hydrolysis.

Discoloring or deodorizing steps can also be added.

The extract can then optionally be combined with a support and dried in order to be presented in solid form.

The steps of the methods described above, taken individually, are usual in the field of extraction of active ingredients from natural raw materials and a person skilled in the art is able to adjust the reaction parameters based on their general knowledge.

The active ingredient according to the invention is particularly effective for cosmetic, non-therapeutic treatment.

The invention therefore also relates to the use of a cosmetic active ingredient as described above or a composition containing said active ingredient in a cosmetic treatment for topical application to the skin, in particular for improving the quality of the skin and specifically for enhancing the radiance of the complexion. The quality of the skin can be defined in particular by three criteria:

an intact mechanical barrier function;
and an unaltered immune barrier function;
and a balance of the skin microbiota.

Skin of a good quality has a radiant complexion.

The use according to the invention is preferably intended for mature skin.

The active ingredient according to the invention can in particular be used for:
- regulating the ecology of the skin, and in particular rebalancing the microbiota, preferably of mature skin, in particular:
  - reducing bacterial diversity; and/or
  - decreasing the abundance of the phylum *Proteobacteria* and the genus *Corynebacterium*;
- and/or strengthening the mechanical barrier of the skin, in particular stimulating the production of antimicrobial peptides of the skin;
- and/or strengthening the immune barrier of the skin, in particular stimulating the synthesis of cohesion and differentiation of skin cells and/or reducing insensible water loss from the skin.

The skin is a complex barrier organ which is home to a number of microorganisms (bacteria, fungi, viruses) on its surface. This microflora colonizing the stratum corneum constitutes the skin microbiota. It is acquired at birth and evolves to reach a state of balance in adulthood. Its composition and abundance are influenced by genetics and lifestyle. This guarantees the unique character of the microbiota between individuals that can therefore be qualified as a microbiological imprint. Microorganisms and their host live in perfect harmony. Balanced microbiota is safe and beneficial for its host. Among the diversity of the skin flora, four main groups of bacteria (or phyla) have been characterized: *Actinobacteria, Firmicutes, Proteobacteria* and *Bacteroidetes* with three predominant species: *Corynebacteria, Propionibacteria* and *Staphylococci*.

The microbiota participates in the development and maintenance of the balance of its host. Microorganisms and the skin barrier act in synergy to protect the skin from external attacks. The skin flora plays a fundamental role since it gives the skin immunity and protection against potential pathogenic colonizers.. Today, the skin microbiota is considered to be a real functional unit of the skin which contributes to its health and beauty.

However, this balance is constantly threatened by various factors, intrinsic and extrinsic, which can alter the composition of the microbiota and the barrier function of the skin. This imbalance of the microbiota, or dysbiosis, disrupts microbe-microbe and microbe-host cooperation and can lead to skin disorders. It is therefore essential to maintain the balance of the skin's ecosystem to display exceptional skin quality.

In order to study the relationship between aging and skin microbiota, the applicants compared the microbiomes of young and mature Caucasian skin (see the evaluation of the effect of the active ingredient according to the invention) by means of meta-sequencing. In volunteers with mature skin, this unprecedented modeling has demonstrated:
- greater bacterial diversity;
- a significant reduction in the phylum *Actinobacteria* in favor of *Proteobacteria*; and
- a significant increase in the genus *Corynebacterium*.

Advantageously, the active ingredient according to the invention is capable of acting on the skin microbiota, and in particular of reducing the abundance of:
- the *Proteobacteria* branch; and
- the genus *Corynebacterium*.

Thus, the active ingredient according to the invention is capable of restoring the balance of the microbiota in mature skin in order to obtain a profile like that of young skin.

In addition, the skin and its microbiota work together to prevent the proliferation of pathogenic microorganisms.

The epidermis actively participates in the defense of the skin via the establishment of two barriers:
- a mechanical barrier, which, due to its impermeability, effectively prevents germs from entering. This impermeable character of the barrier is based on the establishment of tight junctions and a rigid corneal envelope which results from optimal keratinocyte differentiation; and
- an immune barrier which involves an innate defense system. Keratinocytes have danger sensors on their surface which give them the ability to detect unwanted microorganisms. This function is provided by proteins from the TLR (Toll-Like Receptors) family. In response to a threat, keratinocytes synthesize antimicrobial peptides which neutralize and eliminate pathogens. Among these key molecules of innate immunity, we find f3-defensins (hBDs) and ribonucleases (RNases). RNase 7 is described in particular for regulating bacteria of the genus *Corynebacterium*.

The "good bacteria" of the microbiota amplify the immune defenses of their host by stimulating the production of antimicrobial peptides by means of keratinocytes. This demonstrates the synergistic collaboration existing between the host and their microbiota. The integrity of the skin depends on this synergy.

However, with age, these innate defenses are weakened. The vulnerability to pathogenic invasions is increased and impairment of the barrier function appears.

Advantageously, the active ingredient according to the invention is capable of acting on the mechanical and immune barriers.

In particular, the active ingredient according to the invention increases the synthesis of three proteins which are markers of the functionality of the skin's mechanical barrier, specifically claudin-1, filaggrin and loricrin, and also makes it possible to reduce insensible water loss which is characteristic of an improvement in the mechanical barrier function of the skin. In addition, the active ingredient according to the invention also enhances the effectiveness of the immune barrier in vitro. The active ingredient according to the invention also increases the synthesis of the TLR2 danger sensor and the antimicrobial peptides β-defensin 2 (hBD2), β-defensin 3 (hBD3) and riboNuclease 7 (RNase 7), which shows that said active ingredient is capable of restoring the innate immunity of the skin during aging, an essential element for the balance of the microbiota.

By restoring the functionality of the skin's immune and mechanical barriers, which are particularly weakened with age, the active ingredient according to the invention rebalances the microbiota of mature skin. The rebalancing and protective actions of said active ingredient lead to an improvement in the quality of the skin.

Indeed, it enhances the radiance of the complexion by increasing the brightness of the skin and the pink color. The skin is lastingly nourished and is more luminous with less imperfections. The active ingredient according to the invention is preferably used in compositions, these compositions comprising a cosmetically acceptable medium. The compositions are in different galenical forms, suitable for topical application to the skin.

These compositions may be in particular in the form of oil-in-water emulsions, water-in-oil emulsions, multiple emulsions (water/oil/water or oil/water/oil) which may optionally be microemulsions or nanoemulsions, or in the form of solutions, suspensions, hydrodispersions, aqueous gels or powders. They can be more or less fluid and have the appearance of creams or gels or any other appearance of skin care cosmetics.

They may be compositions comprising at least 0.5% *Metschnikowia reukauffi* extract according to the present invention, preferably between 0.5 and 10%.

These compositions comprise, in addition to the active ingredient, a physiologically acceptable and preferably cosmetically acceptable medium, i.e. one which does not cause feelings of discomfort that are unacceptable to the user such as redness, tightness or tingling.

As an additive, the compositions according to the invention may contain at least one compound selected from:
- oils which can be chosen in particular from linear or cyclic, volatile or non-volatile silicone oils;
- waxes such as ozokerite, polyethylene wax, beeswax or carnauba wax;
- silicone elastomers;
- surfactants, preferably emulsifiers, whether non-ionic, anionic, cationic or amphoteric;
- co-surfactants such as linear fatty alcohols;
- thickeners and/or gelling agents;
- humectants such as polyols like glycerin;
- dyes, preservatives, fillers;
- tighteners;
- sequestrants;
- perfumes;
- and mixtures thereof, without this list being exhaustive.

Examples of such additives are cited in particular in the CTFA Dictionary (*International Cosmetic Ingredient Dictionary and Handbook* published by the *Personal Care Product Council*).

Of course, a person skilled in the art would take care to select any additional compounds, active or non-active, and the quantity thereof such that the advantageous properties of the mixture are not, or not substantially, altered by the addition envisaged.

These compositions are in particular intended to be used to improve the quality of the skin, in particular mature skin, by acting on the functionality of the mechanical and/or immune barriers of the skin and on the balance of the skin microbiota.

The invention thus also relates to a non-therapeutic method, specifically a non-therapeutic cosmetic method for treatment of the skin for an effect of improving and/or enhancing the radiance of the complexion, which method consists of the topical application of a composition comprising an active ingredient according to the invention to the skin, in particular to mature skin, and specifically in order to rebalance the microbiota of mature skin. Preferably, the composition comprising the cosmetic active ingredient according to the invention is applied at least once a day for at least 15 days. Preferably, the composition is a composition according to the invention.

In order to illustrate these cosmetic effects on the quality of the skin, in particular on the radiance of the complexion, the mechanical and immune barrier functions and the skin microbiota, the following examples and test results are presented below.

EXAMPLES

Example 1

Active Ingredient According to the Invention

The active ingredient according to example 1 is obtained by implementing the following steps:
- solubilization of the biomass of *Metschnikowia rekaufii* in water at a rate of 100 g/l;
- enzymatic hydrolysis using a protease;
- heat treatment of the hydrolyzate;
- separation of the soluble and insoluble phases by decantation in order to recover the soluble phase;
- filtrations, using a filter making it possible to eliminate the molecules having a molecular weight greater than 5000 Da;
- sterilizing filtration on 0.22 μm.

The hydrolyzate obtained is in the form of a clear yellow liquid.

It is made up of:
- a dry matter content of 33.5 g/l;
- 52% of peptides by weight of dry matter, (determined by the KJELDAHL method), of which 96% of the peptides have a molecular weight less than or equal to 2000 Da;
- 10% of sugars by weight of dry matter, (determined by the DUBOIS method), all of which are oligosaccharides having a molecular weight less than or equal to 2500 Da;
- 38% ash by weight of dry matter, (determined by weighing the residues from the incineration of the hydrolyzate samples at 550° C. in an electric muffle furnace).

This active ingredient according to the invention is an aqueous solution of a very light yellow color.

Example 2

Active Ingredient According to the Invention

The active ingredient according to example 2 is obtained by implementing the following steps:
- solubilization of the biomass of *Metschnikowia rekaufii* in water at a rate of 100 g/l;
- heat treatment;
- separation of the soluble and insoluble phases by decantation in order to recover the soluble phase;
- filtrations, using a filter making it possible to eliminate the molecules having a molecular weight greater than 5000 Da;
- sterilizing filtration on 0.22 μm.

The active ingredient according to example 2 is in the form of a clear yellow liquid.

It is made up of:
- a dry matter content of 28.9 g/l.
- 56% of peptides by weight of dry matter, (determined by the KJELDAHL method);
- 9% of sugars by weight of dry matter, (determined by the DUBOIS method);
- 17% ash by weight of dry matter, (determined by weighing the residues from the incineration of the hydrolyzate samples at 550° C. in an electric muffle furnace).

Example 3

Composition According to the Invention in the Form of Day Formula

An example of a composition according to the invention in the form of a day formula consists of:

| | | | |
|---|---|---|---|
| A. | Water | | qsp 100% |
| | Preservative | | 1% |
| | Glycerol | | 2% |
| B. | DUB 1632 | (Stéarinerie Dubois) | 3% |
| | DUB MM | (Stéarinerie Dubois) | 1.5% |
| | DUB STGAE30 | (Stéarinerie Dubois) | 3% |
| | DUB ININ | (Stéarinerie Dubois) | 2% |
| | Sophiderm | (Sophim) | 4% |
| | Easynov | (Seppic) | 4% |
| C. | Active ingredient according to the invention | | 2.5% |

The pH of the composition is 6.0. It comes in the form of a fluid, white, odorless, shiny emulsion which is easy to apply and has a soft and slick spread.

The composition can be obtained as follows:
Mix A. Heat in a water bath to 80° C. under the effect of magnetic agitation.
Mix B. Heat in a water bath to 80° C. under the effect of magnetic agitation.
At 80° C., emulsify A in B under the effect of a stator rotor at 1800 rpm.
Add C at 30° C.
Leave under the effect of agitation until completely cooled.

Example 4

Composition According to the Invention in the Form of a Serum Formula

An example of a composition according to the invention in the form of a serum formula consists of:

| | | | |
|---|---|---|---|
| A. | Water | | qsp 100% |
| | Preservative | | 1% |
| | Propylene glycol | | 2% |
| B. | Montanov L | (Seppic) | 2% |
| | Lanol 1688 | (Seppic) | 4% |
| | Montanov 14 | (Seppic) | 1% |
| | DUB 5545 | (Stéarinerie Dubois) | 3.5% |
| C. | Satiaxane CX911 | (Cargill) | 0.6% |
| | Active ingredient according to the invention | | 2.5% |

The pH of the composition is 6.6. It comes in the form of a liquid, white, shiny, odorless emulsion and has a light grip and a fresh and slick spread. Very fast penetration, soft and dry finish, evanescent effect.

The composition can be obtained as follows:
Mix A. Heat in a water bath to 80° C. under the effect of magnetic agitation.
Mix B. Heat in a water bath to 80° C. under the effect of magnetic agitation.
At 80° C., emulsify A in B under the effect of a stator rotor at 2000 rpm.
Add C at 30° C., in the order indicated, under the effect of a stator rotor at 1500 rpm.
Leave under the effect of agitation until completely homogenized.

Example 5

Composition According to the Invention in the Form of a Siliconized Gel

An example of a composition according to the invention in the form of a siliconized gel consists of:

| | | | |
|---|---|---|---|
| A. | Water | | qsp 100% |
| | Preservative | | 1% |
| | Glycerol | | 3% |
| B. | KF 6017 | (Shin Etsu) | 3% |
| | KF 6028 | (Shin Etsu) | 2% |
| | Sepimax Zen | (Seppic) | 0.5% |
| | Sensanov WR | (Seppic) | 3% |
| C. | DC 73310 | (Dow Corning) | 3% |
| | Active ingredient according to the invention | | 2.5% |
| | Simulgel EPG | (Seppic) | 0.3% |

The composition has a pH of 5.2.

The composition is in the form of a shiny, odorless, translucent white gel which has a semi-thick texture, a flexible grip and an excellent, silicone-effect application.

The composition can be obtained as follows:
Mix A. Heat in a water bath to 50° C. under the effect of magnetic agitation, making sure to disperse the preservative well.
Mix B. Homogenize well under the effect of magnetic agitation.
Emulsify A in B under the effect of a stator rotor at 1000 rpm for 10 minutes, then at 2200 rpm until completely homogenized.
Then add C, in the order indicated, still under the effect of a rotor stator.
After a few minutes, reduce the agitation to 1000 rpm.

Example 6

Composition According to the Invention in the Form of a Fluid Emulsified Gel An example of a composition according to the invention in the form of a fluid emulsified gel consists of:

| | | | |
|---|---|---|---|
| A. | Water | | qsp 100% |
| | Preservative | | 1% |
| B. | DUB PGPR | (Stéarinerie Dubois) | 0.5% |
| | DUB RG AE 30 | (Stéarinerie Dubois) | 1% |
| | DUB INID | (Stéarinerie Dubois) | 0.5% |
| | Montanox 80 | (Seppic) | 0.5% |
| | Sepinov EMT | (Seppic) | 1% |
| | Easynov | (Seppic) | 1.5% |
| C. | DUB Velvet Gum | (Stéarinerie Dubois) | 3% |
| | Active ingedient according to the invention | | 2.5% |
| | DC 200 | (Dow Corning) | 1% |

The pH of the composition is 6.5.

The composition is in the form of a white, shiny, odorless emulsified gel which has a fluid texture, an easy grip, a gentle application and a slick spread.

The composition can be obtained as follows:
Mix A. Heat in a water bath to 80° C. under the effect of magnetic agitation.
Mix B. Heat in a water bath to 80° C. under the effect of magnetic agitation.

Emulsify B in A, under the effect of a stator rotor at 1800 rpm.

When cold, add C, in the order, and agitate under the effect of a stator rotor at 2000 rpm.

Leave under the effect of agitation until completely homogenized.

Examples of Extracts from other Yeasts (outside the Invention) and Analytical Comparison with the Yeast Extract According to the Invention In order to show the specificity of the yeast selected for the active ingredient according to the invention, we carried out a method of extraction identical to that of the invention on two other yeasts:

Saccharomyces cerevisiae, a yeast widely used in cosmetics and food,

Metschnikowia agaves, a yeast of the same genus as that of the invention.

The characteristics of the different extracts are presented in Table 1.

TABLE 1

|  | Active ingredient according to the invention derived from *Metschnikowia rekaufii* | | Extract derived from *Metschnikowia agaves* | | Extract derived from *Saccharomyces cerevisiae* | |
| --- | --- | --- | --- | --- | --- | --- |
| Method of extraction | Solubilization of yeasts in water at a rate of 100 g/l, Enzymatic hydrolysis using a protease, Heat treatment in order to eliminate enzymatic activities, Separation of the soluble and insoluble phases by decantation, Filtrations, Sterilizing filtration | | | | | |
| Appearance | Clear yellow liquid | | Clear yellow liquid | | Yellow opalescent liquid | |
| Dry matter (g/l) | 33.8 g/l | — | 24.3 | — | 18.1 | — |
| Total sugars (g/l) | 2 g/l | 6% | 1.5 | 6% | 1.8 | 10% |
| Total proteins (g/l) (Lowry method) | 7.8 g/l | 23% | 3.6 | 15% | 5.1 | 28% |
| Total proteins (g/l) (Kjeldahl method) | 15.6 g/l | 47% | 8.7 g/l | 36% | 9.6 g/l | 53% |
| Minerals (g/l) | 9.1 g/l | 27% | 7.4 | 30% | 5.2 | 29% |

The chromatograms of the carbohydrate fractions of the two tests on *Metschnikowia agaves* and on *Saccharomyces cerevisiae* were compared with the active ingredient according to the invention. The chromatograms are different. The nature of the saccharide fraction of the three tests is different.

Tests and Results

Demonstration of the Change in the Skin Microbiota during Aging

Samples of the skin microbiota were taken from the face of volunteers using sterile swabs over an area of 10 cm$^2$. Each swab was then frozen and stored before the extraction of DNA. The analysis was carried out by 16S sequencing. The bacterial genomic DNA is extracted from the samples using the DNeasy Power Lyzer Soil kit (Qigen).

Analysis of the diversity of bacteria in the skin of the face was carried out on 34 healthy Caucasian volunteers: 17 young volunteers of an average age of 28 ±3 years, and 17 mature volunteers of an average age of 62 ±5 years.

The diversity of bacteria taken from the skin makes it possible to carry out the Shannon index which takes into account the number of species of bacteria present and their relative abundance. This index provides information on the structure of the sample.

Analysis of the taxonomy of the bacteria in the samples allows them to be classified according to 7 levels: Kingdom, Branch or Phylum, Class, Order, Family, Genus or Species.

The Average Results on Diversity are as Follows:

TABLE 2

|  | Young | Mature |
| --- | --- | --- |
| Diversity/Shannon index | 1.30 ± 0.44 | 1.74 ± 0.35 |

Mature donors show greater diversity than younger donors, as reflected in the significant increase in the Shannon index.

Based on the distribution of bacteria at the branch (phytum) level, the phyta of the bacteria present on the skin are distributed as follows:

TABLE 3

| Distribution of bacteria/Phytum | Young | Mature |
| --- | --- | --- |
| Actinobacteria | 59.2% | 46.7% |
| Bacteroidetes | 1.1% | 2.1% |
| Firmicutes | 35.3% | 36.2% |
| Proteobacteria | 3.5% | 13.9% |
| Other | 0.9% | 1.0% |

It is noted that, as skin ages, there is an increase in the relative abundance of the *Proteobacteria* branch, and a decrease in the relative abundance of the *Actinobacteria* branch.

Furthermore, based on the distribution of bacteria at the genus level, the relative abundance of the genera of bacteria present on the skin is distributed as follows:

TABLE 4

| Distribution of bacteria/genus | Young | Mature |
| --- | --- | --- |
| *Acinetobacter* | 0.5% | 1.2% |
| *Corynebacterium* | 0.8% | 5.0% |
| *Enhydrobacter* | 0.8% | 3.4% |
| *Propionibacterium* | 56.6% | 40.6% |
| *Staphyloccocus* | 32.2% | 31.5% |

TABLE 4-continued

| Distribution of bacteria/genus | Young | Mature |
|---|---|---|
| Streptococcus | 1.4% | 1.0% |
| Other | 7.7% | 17.3% |

It is thus found that, as the skin ages, there is an increase in the relative abundance of the genus *Corynebacterium*, and a decrease in the relative abundance of the genus *Propionibacterium*. The increase in the proportion of *Proteobacteria* and *Corynebacteria* with age reflects that it is easier for these opportunistic bacteria to colonize the skin during aging.

Demonstration of the Effect of the Active Ingredient According to the Invention on the Skin Microbiota Twice a day, 34 healthy Caucasian volunteers applied a cosmetic formula to the face that contains 2.5% of the active ingredient according to the invention (example 1) and a placebo cosmetic formula to the hemiface. The skin microbiota samples were taken before and after 28 days of cosmetic treatment.

The 34 volunteers are distributed as follows: 17 young volunteers of an average age of 28±3 years, and 17 mature volunteers of an average age of 62±5 years.

The diversity of bacteria taken from the skin makes it possible to carry out the Shannon index which takes into account the number of species of bacteria present and their relative abundance. This index provides information on the structure of the sample.

The abundance of different bacterial taxa is provided in relative abundance. 7 levels of taxonomy are used in the official classification for the classification of bacterial species: Kingdom, Branch or Phylum, Class, Order, Family, Genus or Species. The taxonomic analysis of this study was carried out at two levels of the classification: the branch and the genus. 4 branches: *Actinobacteria, Bacteroidetes, Firmicutes* and *Proteobacteria* and 6 bacterial genera: *Acinetobacter, Corynebacterium, Enhydrobacter, Propionibacterium, Staphyloccocus* and *Streptococcus* are mainly found in the skin microbiota and presented in this study. The other taxa are grouped in the category "other."

The Average Results on Diversity are as Follows:

TABLE 5

| Shannon index | Treatment using active ingredient according to the invention | |
|---|---|---|
| | Young | Mature |
| J0 | 1.33 ± 0.44 | 1.70 ± 0.47 |
| J28 | 1.32 ± 0.53 | 1.51 ± 0.40 |
| Variation J28 − J0 | −1% not significant | −11% |

Mature donors show greater diversity than young donors, reflected by the significant increase in the Shannon index.

The placebo formulation does not modify the diversity of the skin microbiota of mature skin or young skin.

The formulation containing the active ingredient acts on the diversity of the skin microbiota of mature skin by significantly reducing the Shannon index by 11%. However, it does not modify the diversity and the bacterial ecology of young donors.

Figure 1:
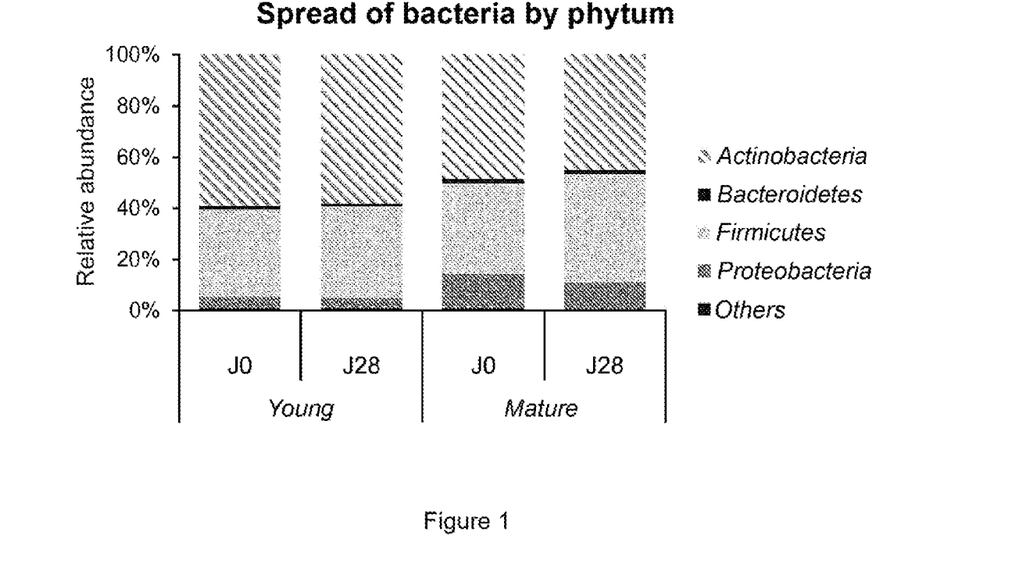
FIG. 1 shows the distribution by phytum of the bacteria present on young and mature skin before and after 28 days of treatment using an active ingredient according to the invention.

Based on the distribution of bacteria at the branch (phylum) level, the phyta of bacteria present on the skin are distributed as shown in FIG. 1 and in Table 6.

TABLE 6

| Distribution of bacteria/phytum | | Treatment using active ingredient according to the invention | |
|---|---|---|---|
| | | Young | Mature |
| Proteobacteria | J0 | 4.4% | 13.3% |
| | J28 | 4.1% | 10.6% |
| | Δ(J28 − J0) | −7% not significant | −20% |

The microbiota of mature donors has a greater abundance of the *Proteobacteria* branch compared to the microbiota of young donors.

The active ingredient according to the invention acts on the composition of the skin microbiota by significantly reducing the abundance of the Proteobacteria branch by 20%. It does not significantly modify the skin microbiota of young skin.

Figure 2:
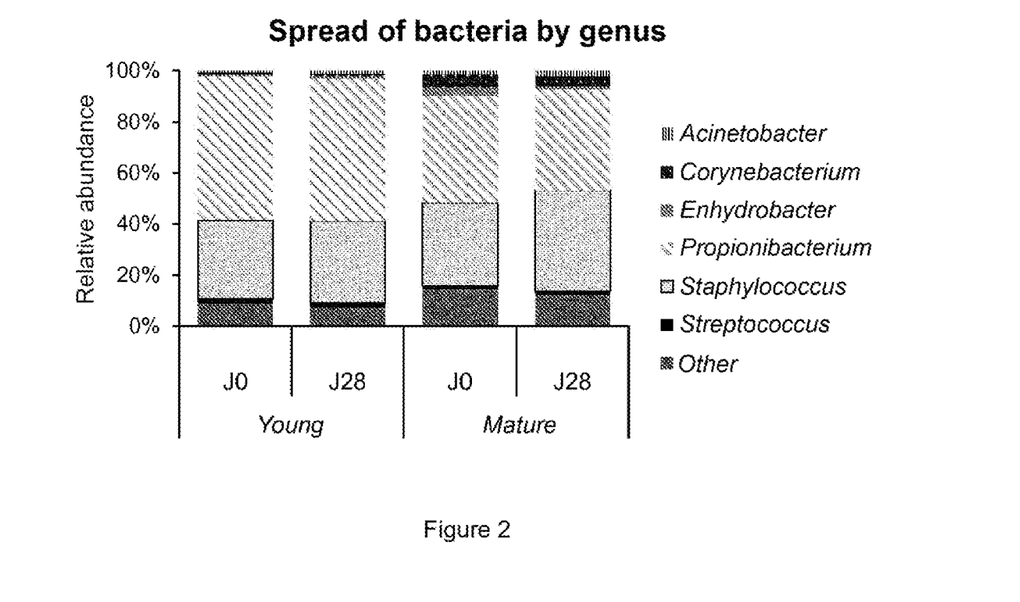
FIG. 2 shows the distribution by genus of the bacteria present on young and mature skin before and after 28 days of treatment using an active ingredient according to the invention.

Based on the distribution of bacteria at the genus level, the genera of bacteria present on the skin are distributed as shown in FIG. 2 and in Table 7.

TABLE 7

| Distribution of bacteria/phytum | | Treatment using active ingredient according to the invention | |
|---|---|---|---|
| | | Young | Mature |
| Corynebacterium | J0 | 0.7% | 5.2% |
| | J28 | 0.9% | 4.1% |
| | Δ(J28 − J0) | +29% | −21% |

The microbiota of mature donors has a higher abundance of the *Corynebacterium* genus compared to the microbiota of young donors.

The active ingredient according to the invention acts on the composition of the skin microbiota by significantly reducing the abundance of the genus *Corynebacterium* by 21%. It does not significantly modify the composition of the microbiota of young skin.

Demonstration of the Effect of *Metschnikowia reukaufii* Extract on the Immune Barrier Function The influence of the active ingredient according to the invention on the immune barrier function was evaluated in three studies:

in vitro on human keratinocyte cultures in order to determine the expression of antimicrobial peptides HBD2;

in vitro on aged reconstructed epidermis (aged Silabskin® RE), in order to assess the expression of TLR2, antimicrobial peptides HBD2 and HBD3, and the antimicrobial protein RNAse 7;

in vivo on 15 healthy volunteers, in order to determine the expression of the ribonuclease 7 (RNAse 7) antimicrobial protein.

The operating procedures for the tests are described below.

Expression of Antimicrobial Peptides HBD2

Normal human keratinocytes are cultured in a specific culture medium and are treated with 1% of the active ingredient according to the invention or other yeast extracts (*Metschnikowia agaves* or *Saccharomyces cerevisiae* as presented in the examples). Total RNA is extracted from keratinocytes after treatment. PCR analysis made it possible to determine the mRNAs of HBD2.

Expression of TLR2, Antimicrobial Peptides HBD2 and HBD3, and the Antimicrobial Protein RNAse 7

The reconstructed epidermis was created using normal or aged human keratinocytes by means of successive passages. The reconstructed epidermis was treated using 0.25% or 0.5% of the active ingredient according to the invention. After 24 hours of treatment, the epidermis was recovered in order to extract the total RNA coding for HBD2, HBD3, TLR2 or RNAse 7.

Expression of Ribonuclease 7 (RNAse 7) Antimicrobial Protein.

The 15 volunteers were treated with a cosmetic formulation containing 2.5% of the active ingredient according to the invention for 14 days of twice-daily applications to the forearms. The determination of RNAse 7 by means of ELISA assay was carried out following a mechanical attack on the skin by means of stripping.

The results for the expression of HBD2 on cultures of human keratinocytes are presented in Table 8:

TABLE 8

|  | HBD2 expression | Ability to induce HBD2 expression |
|---|---|---|
| Witness | 100% |  |
| Treated with 1% of the active ingredient according to the invention of example 1 | 144% | 44% |
| Treated with 1% of Metschnikowia agaves extract | 88% | 0% |
| Treated with 1% of Saccharomyces cerevisiae extract | 80% | 0% |

It has been found that only the active ingredient according to the invention stimulates the expression of HBD2 in human keratinocyte cultures. The two extracts from two other yeasts (Metschnikowia agaves or Saccharomyces cerevisiae) do not have the same effectiveness. We can therefore conclude that only the extract of the selected Metschnikowia rekaufii yeast has an effect on the skin microbiota.

The results for the reconstructed epidermis in order to evaluate the expression of TLR2, antimicrobial peptides HBD2 and HBD3, and the antimicrobial protein RNAse 7 are as follows:

TABLE 9

|  | TLR2 expression | Ability to induce TLR2 expression |
|---|---|---|
| Normal reconstructed epidermis | | |
| Witness | 100% |  |
| Aged reconstructed epidermis | | |
| Witness | 39% |  |
| Treated with 0.25% of the active ingredient according to the invention | 42% | 5% |
| Treated with 0.5% of the active ingredient according to the invention | 62% | 37% |

TABLE 10

|  | HBD2 expression | Ability to induce HBD2 expression |
|---|---|---|
| Normal reconstructed epidermis | | |
| Witness | 100% |  |
| Aged reconstructed epidermis | | |
| Witness | 33% |  |
| Treated with 0.25% of the active ingredient according to the invention | 50% | 26% |
| Treated with 0.5% of the active ingredient according to the invention | 118% | 127% |

TABLE 11

|  | HBD3 expression | Ability to induce HBD3 expression |
|---|---|---|
| Normal reconstructed epidermis | | |
| Witness | 100% |  |
| Aged reconstructed epidermis | | |
| Witness | 47% |  |
| Treated with 0.25% of the active ingredient according to the invention | 51% | 8% |
| Treated with 0.5% of the active ingredient according to the invention | 64% | 32% |

TABLE 12

|  | RNAse 7 expression | Ability to induce RNAse 7 expression |
|---|---|---|
| Normal reconstructed epidermis | | |
| Witness | 100% |  |
| Aged reconstructed epidermis | | |
| Witness | 60% |  |
| Treated with 0.25% of the active ingredient according to the invention | 64% | 9% |
| Treated with 0.5% of the active ingredient according to the invention | 74% | 35% |

Tested at 0.5%, the active ingredient according to the invention significantly increases the expression of antimicrobial peptides, such as beta-defensin 2, beta-defensin 3, TRL2 and RNAse 7, in reconstructed epidermis.

The results for volunteers in order to determine the expression of ribonuclease 7 (RNAse 7) are as follows:

TABLE 13

|  | Average RNAse 7 concentration | Δ/ZNT | Δ/placebo |
|---|---|---|---|
| Untreated area | 0.637 |  |  |
| Placebo | 1.222 | +92% |  |
| Active ingredient according to the invention at 2.5% | 1.978 | −211% | +119% |

After a treatment of 14 days and in comparison with the placebo, the active ingredient according to the invention, formulated at 2.5% in emulsified gel, promotes the release of antimicrobial peptide RNAse 7, of which the broad spectrum of activity of contributes to the skin's defense system.

The active ingredient according to the invention boosts the secretion of RNAse 7 by 119%. This effect is observed in 87% of volunteers.

The active ingredient according to the invention therefore boosts the anti-microbial peptides of the skin.

Demonstration of the Effect of *Metschnikowia reukaufii* Extract on the Mechanical Barrier Function The influence of the active ingredient according to the invention on the mechanical barrier function was evaluated in two studies:

- in vitro on aged reconstructed epidermis (aged Silabskin® RE) in order to assess the expression of tight junctions: claudin-1 and keratinocyte differentiation: filaggrin and loricrin;
- in vivo on 20 healthy Caucasian volunteers in order to determine insensible water loss;
- in vivo on 31 healthy Asian volunteers in order to determine insensible water loss.

The reconstructed epidermis was created using normal or aged human keratinocytes by means of successive passages. The reconstructed epidermis was treated using 0.25% of the active ingredient according to the invention. After 24 hours of treatment, the epidermis was recovered in order to extract the total RNA coding for claudin-1, filaggrin and loricrin.

The volunteers were treated with a cosmetic formulation containing 2.5% of the active ingredient according to the invention for 28 days of twice-daily application to the forearms. Insensible water loss was measured using a Tewameter.

The results for the reconstructed epidermis in order to assess the expression of tight junctions: claudin-1, and for keratinocyte differentiation: filaggrin and loricrin, are as follows:

TABLE 14

|  | Claudin-1 expression (UA) | Ability to induce Claudin-1 expression |
|---|---|---|
| Normal reconstructed epidermis | | |
| Witness | 60.7 | |
| Aged reconstructed epidermis | | |
| Witness | 48.6 | |
| Treated with 0.25% of the active ingredient according to the invention (example 1) | 61.0 | +103% |

TABLE 15

|  | Filaggrin expression (UA) | Ability to induce filaggrin expression |
|---|---|---|
| Normal reconstructed epidermis | | |
| Witness | 27.8 | |
| Aged reconstructed epidermis | | |
| Witness | 22.8 | |
| Treated with 0.25% of the active ingredient according to the invention (example 1) | 27.2 | +90% |

TABLE 16

|  | Loricrin expression (UA) | Ability to induce Loricrin expression |
|---|---|---|
| Normal reconstructed epidermis | | |
| Witness | 29.9 | |
| Aged reconstructed epidermis | | |
| Witness | 15.7 | |
| Treated with 0.25% of the active ingredient according to the invention (example 1) | 21.1 | +38% |

Tested at 0.25% on reconstructed aged epidermis, the active ingredient according to the invention significantly increases the synthesis of claudin-1 by 103%, of filaggrin by 90% and of loricrin by 38%.

The favorable effect on the barrier function has been confirmed in vivo on both Caucasian and Asian skin. Compared to the placebo, the active ingredient according to the invention makes it possible to reduce insensible water losses on the Caucasian panel by 9.1%, and by 9.2% on the Asian panel.

The active ingredient according to the invention therefore contributes well to the restoration of a functional mechanical barrier function.

Demonstration of the Effect of *Metschnikowia reukaufii* Extract on the Radiance of the Complexion The influence of the active ingredient according to the invention on the radiance of the complexion on volunteers was evaluated on two panels:

- a panel of 20 Caucasian volunteers; and
- a panel of 31 Asian volunteers.

The volunteers were treated using a cosmetic formulation containing 2.5% of the active ingredient according to the invention (example 1) for 28 days of twice-daily application to the face.

The radiance of the complexion is evaluated by means of clinical scoring by experts.

On the Caucasian panel, after 28 days of twice-daily application, the active ingredient according to the invention significantly increases the radiation of the skin by 9.5% and pink color by 13.0%. It also significantly reduces olive color by 9.3% and tiredness of the eyes by 8.0%. On the Asian panel, the radiance of the complexion was evaluated by mean of clinical scoring. After 28 days of twice-daily application, the active ingredient according to the invention increases the luminosity of the skin by +12.2%, radiance of the skin by +9.2% and transparency of the skin by +8.2%.

The active ingredient according to the invention is perceived by Caucasian and Asian volunteers as more effective than the placebo. In general, volunteers judged their skin to be sustainably nourished. They found that the active ingredient according to the invention improves the luminosity of their skin and limits imperfections.

The invention claimed is:

1. A cosmetic treatment method comprising applying topically to skin a cosmetic active ingredient or a composition containing said active ingredient; wherein the application is for improving the quality of the skin, enhancing the radiance of the complexion, rebalancing the microbiota of mature skin, reducing bacterial diversity, decreasing abundance of bacteria of the phylum *Proteobacteria* and/or reducing abundance of bacteria of the genus *Corynebacterium*; and wherein the cosmetic active ingredient comprises at least one *Metschnikowia reukaufii* extract comprising peptides, wherein said at least one *Metschnikowia reukaufii* extract is a heat-treated and/or enzymatically treated hydrolysate, wherein the peptides represent at least 20 wt. % dry matter of the extract, wherein the peptide content is determined by the KJELDAHL method.

2. The cosmetic treatment method of claim 1, wherein applying topically to the skin the cosmetic active ingredient or the composition strengthens the mechanical barrier and/or the immune barrier of the skin.

3. The cosmetic treatment method according to claim 2, wherein the method is performed for stimulating the production of antimicrobial peptides in the skin.

4. The cosmetic treatment method according to claim 2, wherein the method is performed for stimulating cohesion and differentiation of skin cells and/or for reducing insensible water loss from the skin.

5. The cosmetic method of claim 1, wherein the composition comprises at least 0.5 wt. % of the active ingredient.

6. The cosmetic method of claim 5, wherein the composition is in the form of a cream or gel.

7. The cosmetic treatment method of claim 1, wherein the skin is mature skin.

8. The cosmetic treatment method of claim 1, wherein the treatment rebalances the microbiota of mature skin.

9. The cosmetic treatment method of claim 1, wherein the cosmetic active ingredient comprises peptides ranging between 20 and 60 wt. % dry matter of the extract, wherein the peptide content is determined by the KJELDAHL method.

10. The cosmetic treatment method of claim 1, wherein the cosmetic active ingredient is characterized in that the *Metschnikowia reukaufii* extract comprises peptides of which at least 90% have a molecular mass of less than 3500 Da.

11. The cosmetic treatment method of claim 1, wherein the active ingredient is characterized in that the *Metschnikowia reukaufii* extract comprises peptides of which at least 60% have a molecular mass of less than 2000 Da.

12. The cosmetic treatment method of claim 1, wherein the cosmetic active ingredient is characterized in that the *Metschnikowia reukaufii* extract also comprises sugars.

13. The cosmetic treatment method of claim 12, wherein the cosmetic active ingredient is characterized in that the sugars comprise glucose and mannose in the form of oligosaccharides having an average molar mass of less than 9000 Da.

* * * * *